United States Patent [19]
Torrens-Jover et al.

[11] Patent Number: 6,118,009
[45] Date of Patent: Sep. 12, 2000

[54] PROCESS FOR OBTAINING ENANTIOMERS OF CIS-OLIRTINE

[75] Inventors: Antoni Torrens-Jover; Jordi Frigola-Constansa, both of Barcelona, Spain

[73] Assignee: Laboratorios Del Dr. Esteve, S.A., Barcelona, Spain

[21] Appl. No.: 09/485,023

[22] PCT Filed: Jul. 31, 1998

[86] PCT No.: PCT/ES98/00223

§ 371 Date: Feb. 1, 2000

§ 102(e) Date: Feb. 1, 2000

[87] PCT Pub. No.: WO99/07684

PCT Pub. Date: Feb. 18, 1999

[30] Foreign Application Priority Data

Aug. 4, 1997 [ES] Spain ..................................... 9701728

[51] Int. Cl.[7] ................................................ C07D 231/12
[52] U.S. Cl. .......................................................... 548/375.1
[58] Field of Search ........................................... 548/375.1

[56] References Cited

FOREIGN PATENT DOCUMENTS

| 305180 | 3/1989 | European Pat. Off. . |
| 9323408 | 11/1993 | WIPO . |
| 9529146 | 11/1995 | WIPO . |

OTHER PUBLICATIONS

Bioorganic & Medicinal Chemistry Letters, vol. 3, N° –2, pp. 269–272, 1993. J.A. Hueso–Rodriguez etal., "Preparation of the Enantiomers Cited in the Analgesic E–3710".

*Primary Examiner*—Robert W. Ramsuer
*Attorney, Agent, or Firm*—Ladas & Parry

[57] ABSTRACT

The procedure comprises (a) the enantioselective reduction of a pro-chiral ketone (III) by using a reducing and agent and chiral catalyst, both boron derivatives, in an anhydrous solvent or mixture of anhydrous solvents to form an enantiomer of an alcohol (II), and (b), the alkylation of (II), in phase transfer conditions, with optionally prior isolation and purification thereof, with 2-chloro-N,N-dimethylethylamine, to form an enantiomer of (I). Cyzolirtine exhibits analgesic properties.

14 Claims, No Drawings

PROCESS FOR OBTAINING ENANTIOMERS OF CIS-OLIRTINE

This application is a 371 of PCT/ES98/00223, filed Jul. 31, 1998.

DESCRIPTION

1. Field of the Invention

This invention refers to a new procedure for obtaining the enantiomers of cyzolirtine, (±)-2-[phenyl(1-methyl-1H-pyrazol-5-yl)methoxy]-N,N-dimethylethanamine, that consists of a sequential process of asymmetric reduction of a ketone followed by alkylation of the alcohol formed.

2. Background of the Invention

The racemic mixture (±)-2-[phenyl(1-methyl-1H-pyrazol-5-yl)methoxy]-N,N-dimethylethanamine (cyzolirtine), of formula I,

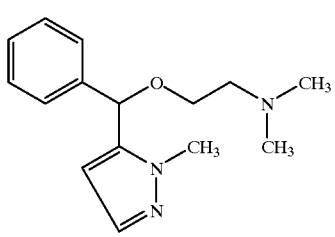

(I)

described in the European patent EP 289 380, shows analgesic properties and currently is in a phase of clinical trials. The two enantiomers of the compound of formula (I) have been synthesised and their analgesic properties evaluated [J. A. Hueso, J. Berrocal, B. Gutierrez, A. J. Farre and J. Frigola, Biorg. Med. Chem. Lett. 1993, 3, 269]. It was found that the dextro-rotatory enantiomer was the most active.

The enantiomers, whose formulae are (+)-I and (−)-I, were obtained by O-alkylation of the enantiomers of formulae (+)-II and (−)-II respectively,

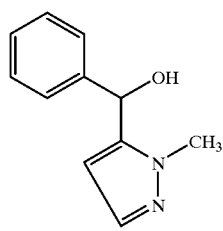

(II)

The enantiomer of formula (+)-II has been obtained by synthesis with very low yields, using (−)-ethyl madelate, allowing the absolute configuration (R) to be assigned to the compound of formula (+)-II. The enantiomers of formula II have also been obtained from laborious processes of separation, by column chromatography or by fractionated crystallisation, of the diastereoisomeric esters formed by reaction of the compound of formula (+)-II with (+)-O-acetylmandelic acid. The yields obtained were 22% for the enantiomer of formula (−)-II and 25% for the enantiomer of (+)-II [J. A: Hueso, J. Berrocal, B. Gutierrez, A. J. Farre and J. Frigola, Bioorg. Med. Chem. Lett. 1993, 3, 269].

On the other hand, during the last few years, obtaining enantiomers by asymmetric synthesis has become an important synthesis method. The asymmetric or enantioselectivity synthesis methods are very abundant and have been extensively described [a) for a treatment of this topic see Morrison, Asymmetric Synthesis, 5 vols., Academic Press: New York, 1983–1985. b) For books, see Nógrádi, Stereoselective Synthesis, VCH: New York, 1986; Eliel, Otsuka, Asymmetric Reactions and Processes in Chemistry, American Chemical Society: Washington, 1982; Morrison, Mosher, Asymmetric Organic Reactions, Prentice-Hall: Englewood Cliffs, N.J., 1971; Izumi, Tai, Stereo-Differentiating Reactions, Academic Press: New York, 1977. c) For reviews see Ward, Chem. Soc. Rev., 1990, 19, 1; Whitesell, Chem. Rev., 1989, 89, 1581; Fujita, Nagao, Adv. Heterocycl. Chem. 1989, 45, 1; Oppolzer, Tetrahedron, 1987, 43, 1969; Seebach, Imwinkelried, Weber, Mod. Synth. Methods, 1986, 4, 125; Mukaiyama, Asami, Top. Curr. Chem., 1985, 127, 133].

The enantioselective reduction of pro-chiral ketones to obtain alcohols with a raised enantiomeric purity is currently the topic of many studies in organic chemistry. [For reviews of the topic see: Brown, Cho, Park, Ramachandran, J Org. Chem., 1987, 52, 5406; Singh, Synthesis, 1992, 605; Brown, Ramachandran, Acc. Chem. Res., 1992, 25, 16; Midland, Morrell, in Houben-Weyl Methods of Organic Chemistry, Helmchen; Hoffmann, Mulzer, Schaumann, Eds. Thieme Verlag: Stuttgart, 1995, Vol. E21d, p4049]. In particular, during the last few years the use of oxazoborolidines as ligands has constituted a very important advance in the asymmetric reduction of ketones. [For recent reviews see: Walbaum and Martens, Tetrahedron: Asymmetry, 1992, 3, 1475; Deloux and Srebnik, Chem. Rev., 1993, 93, 763. See also: Corey, Bakshi, Shibata, Chen, Singh, J. Am. Chem. Soc., 1987, 109, 7925; Franot, Stone, Engeli, Spöndlin, Waldvogel, Tetrahedron: Asymmetry, 1995, 6, 2755 and references therein; Hong, Gao, Nie, Zepp, Tetrahedron Lett., 1994, 35, 6631; Gadja, Tetrahedron: Asymmetry, 1994, 5, 1965; Willems, Dommerholt, Hammink, Vaahost, Thijs, Zwanenburg, Tetrahedron Lett., 1995, 36, 603; Dubois, Fiaud, Kagan, Tetrahedron: Asymmetry, 1995, 6, 1097; Meier, Laux, Tetrahedron, 1996, 52, 589; Schwink, Knochel, Tetrahedron Lett., 1996, 37, 25].

The use of borane as reducing agent and of a chiral 1,3,2-oxazaborolidine as catalyst has been disclosed for the enantioselective reduction of prochiral ketones [EP 0 305 180 A2] as well as for the enantioselective reduction of a-iminoketones [WO 95/29146]. WO 93/23408 discloses some enantioselective oxazaborolidine catalysts useful for the enantioselective reduction of prochiral ketones using a borane reducing agent. However, said documents do not specifically disclose the enantioselective reduction of the pro-chiral ketone phenyl-(1-methyl-1H-pyrazol-5-yl) ketone.

The object of the present invention consists of providing a commercially useful procedure, with a suitable yield and enantiomeric purity, for separately obtaining the dextro-rotatory enantiomer of formula (R)-(+)-I and levo-rotatory enantiomer of formula (S)-(−)-I.

DETAILED DESCRIPTION OF THE INVENTION

The procedure to which the present invention relates is based on a sequential process of asymmetric reduction of the pro-chiral ketone of formula III,

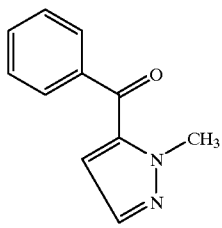

(III)

using an optically active catalyst, to obtain an optically active compound of formula II which, once isolated or without isolation, is submitted to an alkylation reaction to give rise to the formation of the optically active compound of formula (I).

The procedure object of the present invention is based on the reduction of the pro-chiral ketone of formula III to obtain the carbinol of formula II with raised enantiomerical purity and the posterior alkylation of said alcohol, previously isolated or crude (not isolated), with 2-chloro-N,N-dimethylethylamine in phase transfer conditions to give the enantiomers of cyzolirtine (+)-I and (−)-I.

Enantioselective reduction is carried out using reagents derived from boron as reducing agents and chiral oxazaborolidines derived from enantiomerically pure aminoalcohols, as catalysts. In particular, the reducing agents derived from boron used can be diborane, catecolborane, the complexes of boron with THF, borane-dimethylsulphide, borane-1,4oxathiane and other derivatives. The chiral ligands used catalytically between 1% and 50% molar, are oxazoborolidines, derived from optically active aminoalcohols, such as (S)- and (R)-3,3-diphenyl-1-methylpyrrolidine[1,2-c]

Enantioselective reduction is carried out using reagents derived from boron as reducing agents and chiral oxazaborolidines derived from enantiomerically pure aminoalcohols, as catalysts. In particular, the reducing agents derived from boron used can be diborane, catecolborane, the complexes of boron with THF, borane-dimethylsulphide, borane-1,4-oxathiane and other derivatives. The chiral ligands used catalytically between 1% and 50% molar, are oxazoborolidines, derived from optically active aminoalcohols, such as (S)- and (R)-3,3-diphenyl-1-methylpyrrolidine[1,2-c]-1,3,2-oxazaborole [generically known as (S)- and (R)-2-methyl-(CBS)-oxazaborolindine], and its derivatives substituted at the boron atom by alkyl groups, such as (S)- and (R)-3,3-diphenyl-1-butylpyrrolidine[1,2-c]-1,3,2-oxazaborole, or aromatic groups, such as (S)- and (R)-1,3,3-triphenylpyrrolidine[1,2-c]-1,3,2-oxazaborole, (S)- and (R)-2-methyl-4,5,5-triphenyl-1,3,2-oxazaborolidine, (4R, 5S) and (4S, 5R)-5-phenyl-3,4-dimethyl-1,3,2-oxazaborolidine, (4R, 5S)- and (4S, 5R)-5-phenyl-2,4-dimethyl-1,3,2-oxazaboroline, (4R, 5S)- and (4S, 5R)-5-phenyl-4-methyl-1,3,2-oxazaboroline, (4R, 5S)- and (4S, 5R)-5-phenyl-2-methyl-1,3,2-oxazaboroline, among others, that may be commercial, or prepared prior to the reaction or formed "in situ".

The normal procedure consists of mixing the chiral catalyst (between 1% and 50% molar with respect to the keton), the reducing agent (1–10 equivalents) and the ketone of formula III in an anhydrous solvent, such as dichloromethane, toluene, xylene, benzene, pentane, hexane, heptane, petrol ether, 1,4-thioxane, diethyl ether, diisopropyl ether, tetrahydrofuran, 1,4-dioxane, 1,2-dimethoxiethane, and in general any aprotic anhydrous solvent susceptible to being used in a chemical reduction process with boron derivatives, or in a mixture of the aforementioned solvents, toluene being the preferred solvent and toluene/tetrahydrofuran the preferred mixture. Said process can be carried out at temperatures that range between −78° C. and 55° C., the preferred temperatures lying between −18° C. and room temperature. The reaction times vary between 2 and 24 hours.

The alcohol of formula II obtained can be isolated and purified by column chromatography or by crystallisation, or it can be used without prior isolation, using the toluene solution obtained in the reduction process, for the following alkylation reaction in phase transfer conditions. These conditions consist of using an aprotic solvent such as toluene along with an aqueous solution of sodium hydroxide or potassium hydroxide and a quaternary ammonium salt as a catalyst. The mixture is stirred at a temperature between 50° C. and the reflux temperature for a time of between 2 hours and 24 hours.

By way of example, process for obtaining the enantiomers of formula I and its corresponding citrate salts are described, either by isolating the intermediate optically active alcohols of formula II (method A) or without isolating them (method B). These examples are only presented to illustrate the procedure object of the present invention and they should not be taken as limiting its scope.

EXAMPLE 1

Obtaining the citrate of (R)-(+)-2-[phenyl(1-methyl-1H-pyrazol-5-yl)methoxy]-N,N-dimethylethanamine, citrate of (+)-I.

METHOD A

To a solution of (R)-3,3-diphenyl-1-methylpyrrolidine[1,2-c]-1,3,2-oxazaborole 1M in toluene (7.5 ml, 7.5 mmol) cooled to −10° C., under an argon atmosphere, a solution of catecolborane 1M in THF (100 ml, 100 mmol) is added dropwise. To the resulting mixture a solution of phenyl-(1-methyl-1H-pyrazol-5-yl)ketone, III (9.30 g, 50 mmol) in dry toluene is added. Once the addition has been completed the mixture is stirred for 1 hour at −10° C. and then over night at room temperature. Next, MeOH (10 ml) is carefully added while stirring, which is maintained for 6 hours. The reaction mixture is concentrated to half the volume, washed successively with water and with a solution of saturated NaCl, dried and the solvent evaporated to yield an oil which is purified on a silicagel column, eluted with a mixture of ethyl acetate: petrol ether (7:3) to give (R)-(+)-phenyl-(1-methyl-1H-pyrazol-5-yl)methanol, (+)-II (7.82 g, 83%), whose optical purity as determined by chiral HPLC is 99%. M.p. 81–83° C.; $[\alpha]_D$=+16.6 (c=1.0, CHCl$_3$).

Next a mixture of carbinol (+)-II (7.44 g, 40 mmol) dissolved in toluene (80 ml), NaOH 40% (40 ml), tetrabutylamonium bromide (1 g) and 2-chloro-N,N-dimethylethylamine chlorohydrate (11.52 g, 80 mmol) is kept at reflux temperature for 7 hours. The mixture is cooled, the organic layer separated, and the mixture repeatedly washed with water, dried and evaporated to give (R)-(+)-2-[phenyl(1-methyl-1H-pyrazol-5-yl)methoxy]-N,N-dimethylethanamine, (+)-I (9.53 g, 92%). The product obtained is dissolved in ethanol and treated with citric acid monohydrate, crystallising the corresponding citrate of (+)-I (15.42 g) with an optical purity of 99.1%, as determined by chiral HPLC. M.p.129–130° C.; $[\alpha]_D$=+12.3 (c=1.0, CHCl$_3$).

METHOD B

To a solution of (R)-3,3-diphenyl-1-methylpyrrolidine[1,2-c]-1,3,2-oxazaborole 1M in toluene (120 ml, 0.12 mmol)

cooled to 0° C., under an argon atmosphere, a solution of borane-dimethylsulphide 2M in toluene (800 ml, 1.6 mol) is added dropwise. To the resulting mixture a solution of phenyl-(1-methyl-1H-pyrazol-5-yl)ketone, III (148.8 g, 0.8 mmol) in dry toluene (1000 ml) is added. Once the addition has been completed the mixture is stirred for 1 hour at 0° C. and 5 hours at room temperature. Next, MeOH (200 ml) is carefully added and stirring maintained for 6 hours. The reaction mixture is concentrated to half the volume, washed successively with water, a solution of 1M citric acid (2×50 ml) and a saturated solution of NaCl, and dried. The resulting toluene solution is used in the continuation of the synthesis without posterior purification.

Next, a mixture of the toluene solution from the previous step (1600 ml), NaOH 40% (800 ml), tetrabutylamonium bromide (16 g) and 2-chloro-N,N-dimethylethylamine chlorohydrate (184.3 g, 1.6 mmol) is kept at reflux temperature for 7 hours. The mixture is cooled, the organic layer separated, and the mixture repeatedly washed with water, dried and evaporated to give (R)-(+)-2-[phenyl(1-methyl-1H-pyrazol-5-yl)methoxy]-N,N-dimethylethanamine, (+)-I (174.1 g, 84% overall). The product obtained is dissolved in ethanol and treated with citric acid monohydrate, crystallising the corresponding citrate of (+)-I (284.2 g) with an optical purity of 91.9%, as determined by chiral HPLC. M.p.129–131° C.; [α]$_D$=+11.6 (c=1.0, CHCl$_3$).

EXAMPLE 2

Obtaining the citrate of (S)-(+)-2-[Phenyl(1-methyl-1H-pyrazol-5-yl)methoxy]-N,N-dimethylethanamine, citrate of (−)-I.

METHOD A

Following a procedure analogous to method A of example 1, from (S)-3,3-diphenyl-1-methylpyrrolidine[1,2-c]-1,3,2-oxazaborole 1M in toluene (1.5 ml, 1.5 mmol), catecolborane 1M in THF (20 ml, 20 mmol) and phenyl-(1-methyl-1H-pyrazol-5-yl)ketone, III (1.86 g, 10 mmol), (S)-(−)-phenyl-(1-methyl-1H-pyrazol-5-yl)methanol, (−)-II (1.58 g, 84%) is obtained, whose optical purity as determined by chiral HPLC is 98.9%. M.p.: 80–83° C.; [α]$_D$=−16.2 (c=1.0, CHCl$_3$). Said carbinol (1.50 g) is alkylated by means of a phase transfer process analogous to that described earlier, then treated with citric acid and re-crystallised in ethanol to give the citrate of (S)-(−)-2-[phenyl(1-methyl-1H-pyrazol-5-yl)methoxy]-N,N-dimethylethanamine, (−)-I (3.27 g, 91%) with an optical purity of 99%, as determined by chiral HPLC. M.p.: 129–131° C.; [α]$_D$=−12.2 (c=1.0, CHCl$_3$).

METHOD B

Following a procedure analogous to method A of example 1, from (S)-1,3,3-diphenyl-1-methylpyrrolidine[1,2-c]-1,3, 2-oxazaborole 1M in toluene (120 ml, 0.12 mmol), borane-dimethylsulphide 2M in in toluene (20 ml, 40 mmol) and phenyl-(1-methyl-1H-pyrazol-5-yl)ketone, III (3.72 g, 20 mmol) a crude carbinol is obtained dissolved in toluene, which is alkylated without posterior purification by means of a phase transfer process analogous to that described earlier, then treated with citric acid and re-crystallised in ethanol to obtain the citrate of (S)-(−)-2-[phenyl(1-methyl-1H-pyrazol-5-yl)methoxy]-N,N-dimethylethanamine, with an optical purity of 92%, as determined by chiral HPLC. M.p.: 128

What is claimed is:

1. A procedure for obtaining the enantiomers of cyzolirtine, (±)-2-[phenyl(1-methyl-1H-pyrazol-5-yl) methoxy]-N,N-dimethylethanamine, of formula I,

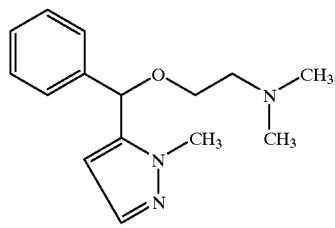

that comprises the enantioselective reduction of the pro-chiral ketone of formula III

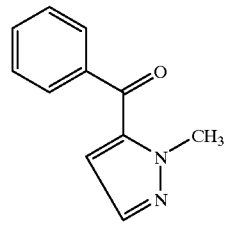

using a borane reducing agent and a chiral catalyst derived from boron selected from a chiral oxazaborolidine, in an anhydrous solvent or mixture of anhydrous solvents at temperatures lying between −78° C. and 55° C., to form an enantiomer of the alcohol of formula II,

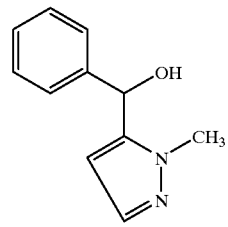

and the alkylation, in phase transfer conditions, of this optically active compound, prior to isolation and purification or without isolation, with 2-chloro-N,N-dimethylethylamine.

2. A procedure, according to claim 1, that consists of performing the asymmetric reduction of the pro-chiral ketone phenyl-(1-methyl-1H-pyrazol-5-yl)ketone of formula III, to give rise to the formation of an enantiomer of formula II, using catecolborane as the reducing agent.

3. A procedure, according to claim 1, that consists of performing the asymmetric reduction of the pro-chiral ketone phenyl-(1-methyl-1H-pyrazol-5-yl)ketone of formula III, to give rise to the formation of an enantiomer of formula II, using borane-dimethylsulphide as the reducing agent.

4. A procedure, according to claim 1, that consists of performing the asymmetric reduction of the pro-chiral ketone phenyl-(1-methyl-1H-pyrazol-5-yl)ketone of formula III, to give rise to the formation of an enantiomer of formula II, using (R)-(+)-3,3-diphenyl-1-methylpyrrolidine [1,2-c]-1,3,2-oxazaborole as a catalyst.

5. A procedure, according to claim 1, that consists of performing the asymmetric reduction of the pro-chiral ketone phenyl-(1-methyl-1H-pyrazol-5-yl)ketone of formula III, to give rise to the formation of an enantiomer of formula II, using (S)-(−)-3,3-diphenyl-1-methylpyrrolidine [1,2-c]-1,3,2-oxazoborole as a catalyst.

6. A procedure, according to claim 1, that consists of performing the asymmetric reduction of the pro-chiral phenyl-(1-methyl-1H-pirazol-5-yl)ketone of formula III, obtaining, isolating and purifying an enantiomer of formula II.

7. A procedure, according to claim 6, that consists of performing the asymmetric reduction of the pro-chiral phenyl-(1-methyl-1H-pirazol-5-yl)ketone of formula III, obtaining, isolating and purifying the enantiomer (R)-(+)-phenyl(1-methyl-1H-pyrazol-5-yl)methanol, (+)-II.

8. A procedure, according to claim 6, that consists of performing the asymmetric reduction of the pro-chiral phenyl-(1-methyl-1H-pirazol-5-yl)ketone of formula III, obtaining, isolating and purifying the enantiomer (S)-(−)-phenyl(1-methyl-1H-pyrazol-5-yl)methanol, (−)-II.

9. A procedure, according to claim 1, that consists of performing the asymmetric reduction of the pro-chiral ketone chiral phenyl-(1-methyl-1H-pirazol-5-yl)ketone of formula III, and without isolating the enantiomer formed, reacting it with 2-chloro-N,N-dimethylethylamine to obtain an enantiomer of cyzolirtine, of formula I.

10. A procedure, according to claim 9, that consists of performing the asymmetric reduction of the pro-chiral ketone chiral phenyl-(1-methyl-1H-pirazol-5-yl)ketone of formula III, and without isolating the enantiomer formed, reacting it with 2-chloro-N,N-dimethylethylamine to obtain the enantiomer (R)-(+)-2-[phenyl(1-methyl-1H-pyrazol-5-yl)methoxy]-N,N-dimethylethanamine, (+)-I.

11. A procedure, according to claim 9, that consists of performing the asymmetric reduction of the pro-chiral ketone chiral phenyl-(1-methyl-1H-pirazol-5-yl)ketone of formula III, and without isolating the enantiomer formed, reacting it with 2-chloro-N,N-dimethylethylamine to obtain the enantiomer (S)-(−)-2-[phenyl(1-methyl-1H-pyrazol-5-yl)methoxy]-N,N-dimethylethanamine, (−)-I.

12. A procedure, according to claim 1, that consists of performing the asymmetric reduction of the pro-chiral ketone chiral phenyl-(1-methyl-1H-pirazol-5-yl)ketone of formula III, in an anhydrous solvent or a mixture of anhydrous solvents.

13. A procedure, according to claim 12, that consists of performing the asymmetric reduction of the pro-chiral ketone chiral phenyl-(1-methyl-1H-pirazol-5-yl)ketone of formula III, in toluene or a mixture of toluene and tetrahydrofuran.

14. A procedure, according to claim 1, that consists of performing the asymmetric reduction of the pro-chiral chiral phenyl-(1-methyl-1H-pirazol-5-yl)ketone of formula III, at temperatures lying between −18° C. and room temperature.

* * * * *